United States Patent
Lee et al.

(10) Patent No.: US 7,909,766 B2
(45) Date of Patent: Mar. 22, 2011

(54) SYSTEMS AND METHODS FOR IMPROVING THE IMAGING RESOLUTION OF AN IMAGING TRANSDUCER

(75) Inventors: Warren Lee, Blacksburg, VA (US); Jian R. Yuan, Hayward, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 1475 days.

(21) Appl. No.: 10/443,592

(22) Filed: May 21, 2003

(65) Prior Publication Data

US 2004/0236205 A1    Nov. 25, 2004

(51) Int. Cl.
*A61B 8/00* (2006.01)
(52) U.S. Cl. ......... 600/462; 600/463; 600/466; 600/472
(58) Field of Classification Search ............ 600/462, 600/463, 466, 472
See application file for complete search history.

(56) References Cited

U.S. PATENT DOCUMENTS

| | | | |
|---|---|---|---|
| 3,005,452 A * | 10/1961 | Pitman | 600/138 |
| 4,349,032 A | 9/1982 | Koyata | |
| 4,387,720 A | 6/1983 | Miller | |
| 4,674,515 A | 6/1987 | Andou et al. | |
| 4,794,931 A | 1/1989 | Yock | |
| 4,815,470 A * | 3/1989 | Curtis et al. | 600/459 |
| 4,821,731 A | 4/1989 | Martinelli et al. | |
| 4,834,102 A * | 5/1989 | Schwarzchild et al. | 600/463 |
| 4,951,677 A | 8/1990 | Crowley et al. | |
| 5,000,185 A | 3/1991 | Yock | |
| 5,024,234 A | 6/1991 | Leary et al. | |
| 5,054,492 A | 10/1991 | Scribner et al. | |
| 5,078,702 A * | 1/1992 | Pomeranz | 604/524 |
| 5,115,814 A | 5/1992 | Griffith et al. | |
| 5,199,437 A * | 4/1993 | Langberg | 600/463 |
| 5,203,338 A | 4/1993 | Jang | |
| 5,243,988 A | 9/1993 | Sieben et al. | |
| 5,249,580 A * | 10/1993 | Griffith | 600/463 |
| 5,305,755 A * | 4/1994 | Nakao | 600/472 |
| 5,368,035 A | 11/1994 | Hamm et al. | |
| 5,400,789 A * | 3/1995 | Griffith | 600/466 |
| 5,438,997 A * | 8/1995 | Sieben et al. | 600/463 |
| 5,509,917 A | 4/1996 | Cecchetti et al. | |
| 5,571,114 A * | 11/1996 | Devanaboyina | 606/108 |
| 5,640,961 A * | 6/1997 | Verdonk | 600/459 |
| 5,655,537 A * | 8/1997 | Crowley | 600/462 |

(Continued)

FOREIGN PATENT DOCUMENTS

EP    0 580 304    1/1994

(Continued)

OTHER PUBLICATIONS

"HDPE (High-Density Polyethylene)". Dec. 2001. http://web.archive.org/web/20011212210839/http://www.jbcplastic.com/hdpe.htm.*

(Continued)

*Primary Examiner* — Tse Chen
*Assistant Examiner* — Peter Luong
(74) *Attorney, Agent, or Firm* — Fommer Lawrence & Haug LLP; Patrick R. Turner

(57) ABSTRACT

The present invention is generally directed towards an imaging transducer assembly. Generally, the imaging transducer assembly includes an imaging transducer located within the lumen of a sheath, wherein the sheath is configured such that an energy beam emitted from the imaging transducer narrows as it exits the sheath, resulting in an image with a higher resolution.

17 Claims, 6 Drawing Sheets

U.S. PATENT DOCUMENTS

| | | | |
|---|---|---|---|
| 5,820,561 A | 10/1998 | Olstad et al. | |
| 5,827,313 A | 10/1998 | Ream | |
| 5,873,830 A | 2/1999 | Hossack et al. | |
| 5,879,305 A | 3/1999 | Yock et al. | |
| 5,897,504 A * | 4/1999 | Buck et al. | 600/463 |
| 5,902,242 A | 5/1999 | Ustuner et al. | |
| 5,902,245 A | 5/1999 | Yock | |
| 5,921,934 A | 7/1999 | Teo | |
| 5,931,788 A | 8/1999 | Keen et al. | |
| 5,979,093 A | 11/1999 | Harruff et al. | |
| 5,980,451 A * | 11/1999 | O'Hara et al. | 600/121 |
| 5,984,871 A | 11/1999 | TenHoff et al. | |
| 5,993,390 A | 11/1999 | Savord et al. | |
| 6,014,473 A | 1/2000 | Hossack et al. | |
| 6,019,724 A | 2/2000 | Gronningsaeter et al. | |
| 6,056,691 A | 5/2000 | Urbano et al. | |
| 6,078,831 A | 6/2000 | Belef et al. | |
| 6,120,455 A | 9/2000 | Teo | |
| 6,123,670 A | 9/2000 | Mo | |
| 6,139,499 A | 10/2000 | Wilk | |
| 6,165,127 A | 12/2000 | Crowley | |
| 6,171,250 B1 | 1/2001 | White et al. | |
| 6,190,320 B1 | 2/2001 | Lelong | |
| 6,248,076 B1 | 6/2001 | White et al. | |
| 6,261,234 B1 | 7/2001 | Lin | |
| 6,261,246 B1 | 7/2001 | Pantages | |
| 6,267,727 B1 | 7/2001 | Teo | |
| 6,283,921 B1 * | 9/2001 | Nix et al. | 600/466 |
| 6,287,261 B1 * | 9/2001 | Suorsa et al. | 600/459 |
| 6,309,379 B1 * | 10/2001 | Willard et al. | 600/467 |
| 6,360,027 B1 | 3/2002 | Hossack et al. | |
| 6,364,840 B1 | 4/2002 | Crowley | |
| 6,419,639 B2 * | 7/2002 | Walther et al. | 600/562 |
| 6,428,477 B1 | 8/2002 | Mason | |
| 6,442,289 B1 | 8/2002 | Olsson et al. | |
| 6,450,964 B1 | 9/2002 | Webler | |
| 6,491,636 B2 | 12/2002 | Chenal et al. | |
| 6,511,426 B1 | 1/2003 | Hossack et al. | |
| 6,516,215 B1 | 2/2003 | Roundhill | |
| 6,520,912 B1 | 2/2003 | Brooks et al. | |
| 6,520,915 B1 | 2/2003 | Lin et al. | |
| 6,524,251 B2 * | 2/2003 | Rabiner et al. | 600/439 |
| 6,529,760 B2 | 3/2003 | Pantages et al. | |
| 6,537,217 B1 | 3/2003 | Bjaerum et al. | |
| 6,540,681 B1 | 4/2003 | Cheng et al. | |
| 2001/0020126 A1 * | 9/2001 | Swanson et al. | 600/407 |
| 2001/0039058 A1 | 11/2001 | Iheme et al. | |
| 2001/0041336 A1 * | 11/2001 | Anderson et al. | 435/6 |
| 2003/0233115 A1 * | 12/2003 | Eversull et al. | 606/194 |

FOREIGN PATENT DOCUMENTS

| | | |
|---|---|---|
| EP | 0 580 304 A1 | 1/1994 |
| JP | 02277445 A2 | 11/1990 |
| JP | 07111996 A2 | 5/1995 |
| JP | 09117452 A2 | 5/1997 |
| JP | 10071149 A2 | 3/1998 |
| JP | 10248850 A2 | 9/1998 |

OTHER PUBLICATIONS

Selfride, Alan. "US data for liquids." Jun. 27, 2002. Sep. 14, 2010. http://web.archive.org/web/20020627114512/http://signal-processing.com/tech/us_data_liquid.htm.*

C.L. de Korte, et al, "High Resolution IVUS Elastography in Patients", Proceedings of the IEEE Ultrasonics Symposium, 2000, pp. 1767-1770, The Netherlands.

Didier Vray, et al., "Synthetic Aperture-Based Beam Compression for Intravascular Ultrasound Imaging", IEEE Transactions on Ultrasonics, Ferroelectrics, and Frequency Control, Jan. 2001, pp. 189-201, vol. 48, No. 1, USA.

Yao Wang, et al., "Optimizing the Beam Pattern of a Forward-Viewing Ring-Annular Ultrasound Array for Intravascular Imaging", Dec. 2002, pp. 1652-1664, vol. 49, No. 12, USA.

* cited by examiner

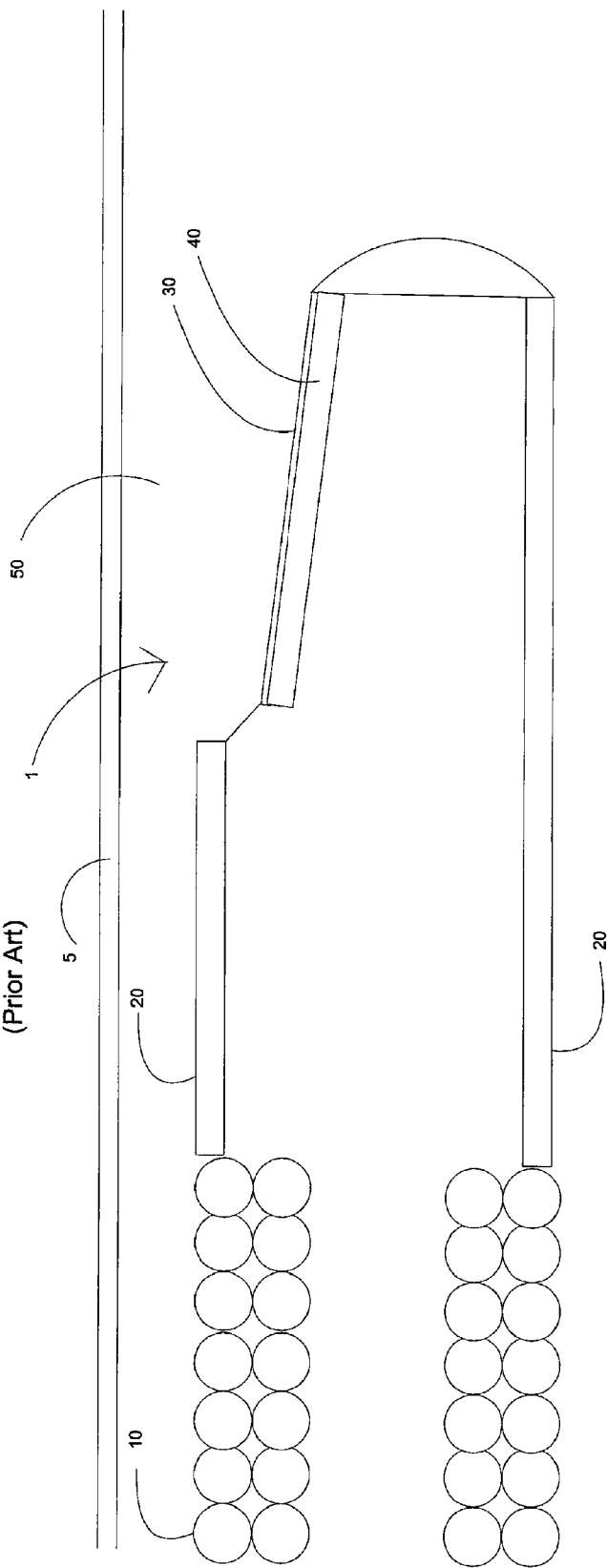
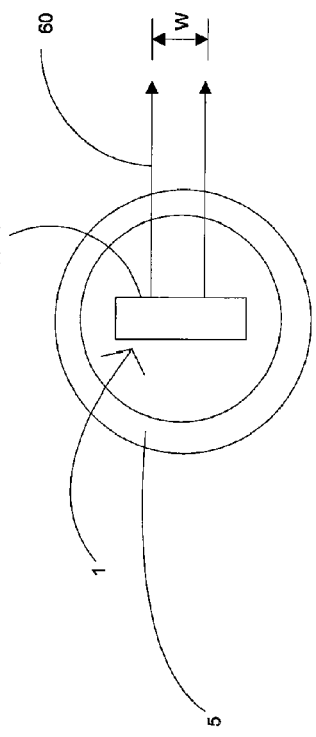
Fig. 1a (Prior Art)
Fig. 1b (Prior Art)

SYSTEMS AND METHODS FOR IMPROVING THE IMAGING RESOLUTION OF AN IMAGING TRANSDUCER

FIELD OF THE INVENTION

The field of the invention relates to medical imaging systems, and more particularly to systems and methods for improving the imaging resolution of an imaging transducer.

BACKGROUND OF THE INVENTION

Intraluminal, intracavity, intravascular, and intracardiac treatments and diagnosis of medical conditions utilizing minimally invasive procedures are effective tools in many areas of medical practice. These procedures are typically performed using imaging and treatment catheters that are inserted percutaneously into the body and into an accessible vessel of the vascular system at a site remote from the vessel or organ to be diagnosed and/or treated, such as the femoral artery. The catheter is then advanced through the vessels of the vascular system to the region of the body to be treated. The catheter may be equipped with an imaging device, typically an ultrasound imaging device, which is used to locate and diagnose a diseased portion of the body, such as a stenosed region of an artery. For example, U.S. Pat. No. 5,368,035, issued to Hamm et al., the entire disclosure of which is incorporated herein by reference, describes a catheter having an intravascular ultrasound imaging transducer.

FIGS. 1a and 1b show an example of an imaging transducer assembly 1 known in the art. The imaging transducer assembly 1 is situated within the lumen 50 of a sheath 5 of a guidewire (partially shown) and is capable of rotating 360° within the sheath 5, about the axis of the sheath 5. The lumen 50 of the sheath 5 is typically filled with a sonolucent liquid, such as water or saline that surrounds the transducer assembly 1. The imaging transducer assembly 1 includes a drive shaft 10 and a stainless steel housing 20 coupled to the distal end of the drive shaft 10, which serves to reinforce the structure of the transducer assembly 1. Toward the distal end of the housing 20 is a layer of piezoelectric crystal ("PZT") 40, attached to an acoustic lens 30 exposed to the sonolucent liquid in the lumen 50.

During operation, the imaging transducer assembly 1 may be placed within a blood vessel at an area where an image is desired, i.e. the imaging environment (not shown). Turning to FIG. 1b, which shows a cross-sectional view of the imaging transducer assembly 1 of FIG. 1a from the distal end, the transducer assembly 1 then emits energy, via the PZT 40 and acoustic lens 30, in the form of acoustic beams 60 out of the sheath 5 and into the area being imaged. One of the purposes of the sheath 5 is to isolate the imaging transducer assembly 1 from the imaging environment yet maintain sonolucense so as to not distort the beams 60. These acoustic beams 60 reflect off targets in the area and then return to the transducer assembly 1. The received reflected beams 60 are then used to generate the desired image. The drive shaft 10 is used to steer and rotate the transducer assembly 1 within the sheath 5. By rotating the transducer assembly 1 by 360°, a complete cross-sectional image of the vessel may be obtained.

The quality of the image depends upon several factors. One of the factors is the width W of the acoustic beams 60. Accordingly, there is a need for an improved imaging device that outputs beams with a narrower width in order to increase the resolution of the image and allows images to be obtained for smaller objects.

SUMMARY OF THE INVENTION

The improved imaging device is intended for use within the lumen of a blood vessel. Generally, the imaging device includes an imaging transducer, capable of emitting one or more energy beams. In one embodiment of the invention, the imaging transducer may be surrounded by a sheath, where the sheath is configured such that when the imaging transducer emits the one or more energy beams, the sheath narrows the width of the one or more energy beams as the one or more energy beams exits the sheath.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the present inventions are obtained, a more particular description of the invention briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

FIG. 1a is a cross-sectional side view of an imaging transducer assembly known in the art.

FIG. 1b is a cross-sectional distal end view of the prior art imaging transducer assembly of FIG. 1a.

DETAILED DESCRIPTION OF THE PREFERRED EMBODIMENTS

Described below are improved imaging devices.

Turning to FIG. 1b, a cross-sectional distal end view of a prior art imaging transducer assembly 1 within the lumen of a sheath 5, having a curvature, is shown. The purpose of the sheath 5 is generally to isolate the transducer assembly 1 from the imaging environment. The sheath 5 is desirably sonolucent so as not to distort the acoustic beams 60 emitted from the transducer assembly 1. Typically, as the beam 60 exits the sheath 5, the width W of the beam 60 remains substantially constant.

Figure 2:
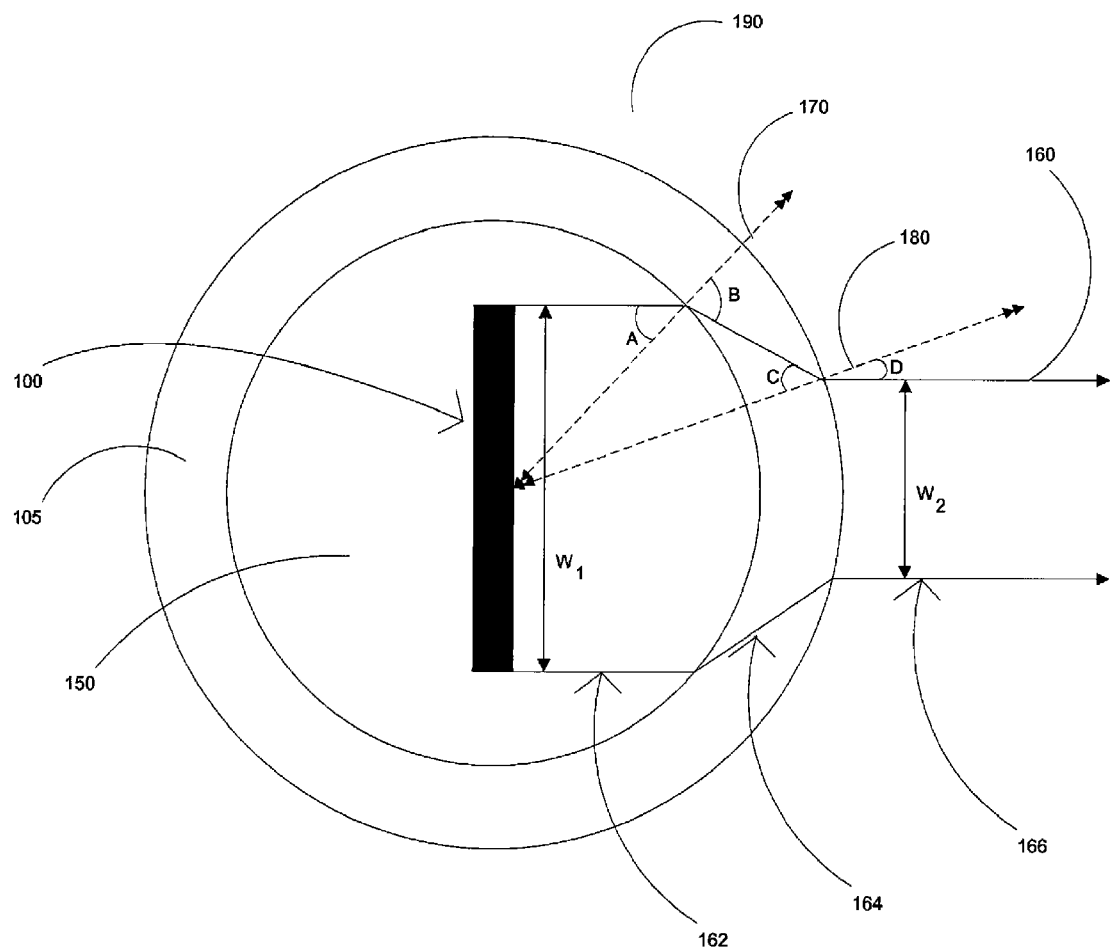
FIG. 2 is a cross-sectional distal end view of an imaging transducer assembly in accordance with an example embodiment of the invention.

To increase the resolution of the image obtained by an imaging transducer assembly, the width W of the beam 60 may be narrowed. One approach to narrowing the acoustic beam emitted from an imaging transducer is shown in FIG. 2, which shows a cross-sectional distal end view of an imaging transducer assembly 100 located within the lumen 150 of a sheath 105. The imaging transducer assembly 100 emits an acoustic beam 160 having a width $W_1$. Instead of the sheath 105 maintaining the width $W_1$ of the beam 160, the sheath 105 is configured to narrow the width of the beam 160 from $W_1$ to $W_2$, as explained in detail below. The narrower width $W_2$ desirably increases the resolution and precision of the resulting image.

The ability to narrow the width $W_1$ of the beam 160 can be explained by using a physics principle known as Snell's Law, which states:

$$n_1 \sin \Theta_1 = n_2 \sin \Theta_2 \text{ wherein,} \quad (1)$$

$n_1$=the refractive index of the incident medium,
$\Theta_1$=the angle of the incidence,
$n_2$=the refractive index in the transmitted medium, and
$\Theta_2$=the angle of refraction.

The refractive index, n, is a constant associated with a particular material, or medium, and indicates how much the medium will refract an energy beam that reaches the surface of the medium. The incident medium is the medium in which the incident energy beam is traveling, and the transmitted medium is the medium in which the refracted energy beam is traveling. Applying these terms to FIG. 2, the incident medium, $n_1$, is the medium within the lumen 150. This is typically a sonolucent medium, such as water or saline. The transmitted medium, $n_2$, is the medium of the sheath 105. A common material, for example, for the sheath 105 is polyethylene ("PE").

The angle of incidence, $\Theta_1$, is measured between the incident energy beam and the normal to the surface between the incident and transmitted mediums. The angle of refraction, $\Theta_2$, is measured between the normal to the surface between the incident and transmitted mediums and the refracted energy beam. Applying these terms to FIG. 2, the angle of incidence is angle A, between the normal 170 to the surface of the inside of the sheath 105, exposed to the lumen 150, and the portion 162 of the energy beam 160 traveling through the lumen 150. Accordingly, the angle of refraction is angle B, between the same normal line 170 and the portion 164 of the beam 160 traveling through the sheath 105.

Likewise, the sheath 105 can also be viewed as the incident medium and the area 190 outside of the sheath 105 can be viewed as the refracted medium. Thus, angle C can be viewed as the angle of incidence, between the normal 180 to the surface of the outside 190 of the sheath 105 and the portion 164 of the beam 160 traveling through the sheath 105. Further, angle D can be viewed as the angle of refraction, between the normal 180 to the surface of the outside 190 of the sheath 105 and the portion 166 of the beam 160 traveling through the medium outside of the sheath 105. As shown in FIG. 2, the refraction occurring at the inside surface of the sheath 105 and the refraction occurring at the outside surface of the sheath 105 result in a narrower beam 160 exiting the sheath 105.

In addition to the refractive index, n, a medium may also be characterized by its phase velocity or sound velocity, v, which is the velocity of propagation of an energy wave, e.g., acoustic wave, traveling through the medium. The phase velocity, v, is inversely proportional to the refractive index, n, and thus, Snell's Law may be represented as:

$$v_2 \sin \Theta_1 = v_1 \sin \Theta_2 \text{ wherein,} \quad (2)$$

$v_2$=the phase velocity of the transmitted medium,
$v_1$=the phase velocity of the incident medium, and
$\Theta_2$=the angle of refraction.

Using equation (1) or (2), if the medium within the lumen 150 is viewed as the incident medium, and the sheath 105 is viewed as the transmitted medium, then if the angle of refraction, $\Theta_2$, within the sheath 105, i.e., angle B, is increased to a value at least greater than angle A, then the acoustic beam 160 will desirably become more narrow, i.e., the value of $W_2$ will be smaller.

There are several approaches to increasing angle B. One approach is to use a sheath 105 material with a higher phase velocity, $v_2$, than the phase velocity of the medium within the lumen 150, $v_1$. Using equation (2), a higher value $v_2$ will result in a higher angle of refraction, $\Theta_2$, and thus, an increased angle B. For example, if water, which typically has a phase velocity of approximately 1.5 mm/μsec, is used as the medium within the lumen 150, then a sheath 105 material with a higher phase velocity, e.g., 2.0 mm/μsec, will result in an increased angle B.

With regard to angles C and D, where angle C is the angle of incidence within the sheath 105 and angle D is the angle of refraction outside 190 of the sheath 105, often the transmitted medium outside 190 of the sheath 105 is blood, which typically has substantially the same phase velocity as water, i.e., 1.5 mm/μsec. Accordingly, if the sheath 105 material has a higher phase velocity than the phase velocity of the medium outside 190 of the sheath 105, then using equation (2), the angle of incidence, angle C, may be larger than the angle of refraction, angle D. However, because of the curvature of the sheath 105, the normal to the surface of the outside 190 of the sheath 105 occurs at 180, and thus, the portion 166 of the beam 160 exiting the sheath 105 is still narrower than the portion 162 of the beam 160 within the lumen 150 of the sheath 105.

A common sheath 105 material includes a mixture of different types of materials, e.g., different types of PE materials. As can be appreciated by one of ordinary skill in the art, the sheath 105 materials may be produced by blending certain percentages of different materials having different densities, such as REXENE®, a polyethylene having a phase velocity of approximately 2.32 mm/μsec and a density of 0.89 g/mm, and ALATHON®, which has a phase velocity of approximately 2.25 mm/μsec and a density of 0.92 g/mm. This may affect the phase velocity $v_2$ of the sheath 105 material. In one example, a sheath 105 material may include 70% REXENE® polyethylene and 30% ALATHON®.

Another approach is to increase the thickness of the sheath 105. An increased thickness may result in moving the normal line 180 to the outside surface of the sheath 105 closer to the center of the beam 160, thus resulting in a narrower beam 160. The thicker sheath 105 may decrease the incident angle within the sheath 105, angle C, and thus decrease the angle of refraction outside 190 of the sheath 105, i.e., angle D. However, because of the change in the normal line 180, the resulting beam thickness $W_2$ will desirably be smaller. The amount of thickness may depend upon the diameter of the sheath 105 and the dimensions of the imaging environment, e.g., the diameter of a blood vessel in which the transducer assembly 100 and sheath 105 is located. For a sheath 105 having a diameter of approximately 1 mm and for a blood vessel having a diameter of at least 6 mm, it may be desirable to have sheath 105 thickness of at least 0.18 mm. In addition, multiple sheath layers may be used (not shown), and further, each layer may have a higher phase velocity than its neighboring inner layer.

In yet another approach, the radius of curvature of the inside surface of the sheath 105 may be decreased. In this approach, the decreased radius of curvature may cause the angle of incidence, $\Theta_1$, i.e., angle A, to increase, which may then, using equation (1) or (2), increase the angle of refraction, $\Theta_2$, within the sheath 105, i.e., angle B. In another approach, a medium within the lumen 150 may be selected or produced with a lower phase velocity, $v_1$. Using equation (2), a medium within the lumen 150 with a lower phase velocity, $v_1$, may result in a higher angle of refraction, $\Theta_2$, within the sheath 105, i.e., angle B. For example, typically, the medium within the lumen 150 is water, which typically has a phase velocity of approximately 1.5 mm/μsec. Other liquids or materials may be used that have lower phase velocities than the phase velocity for water, such as certain types of alcohols, such as ethanol, which has a phase velocity of 1.207 mm/μsec.

Figure 3:
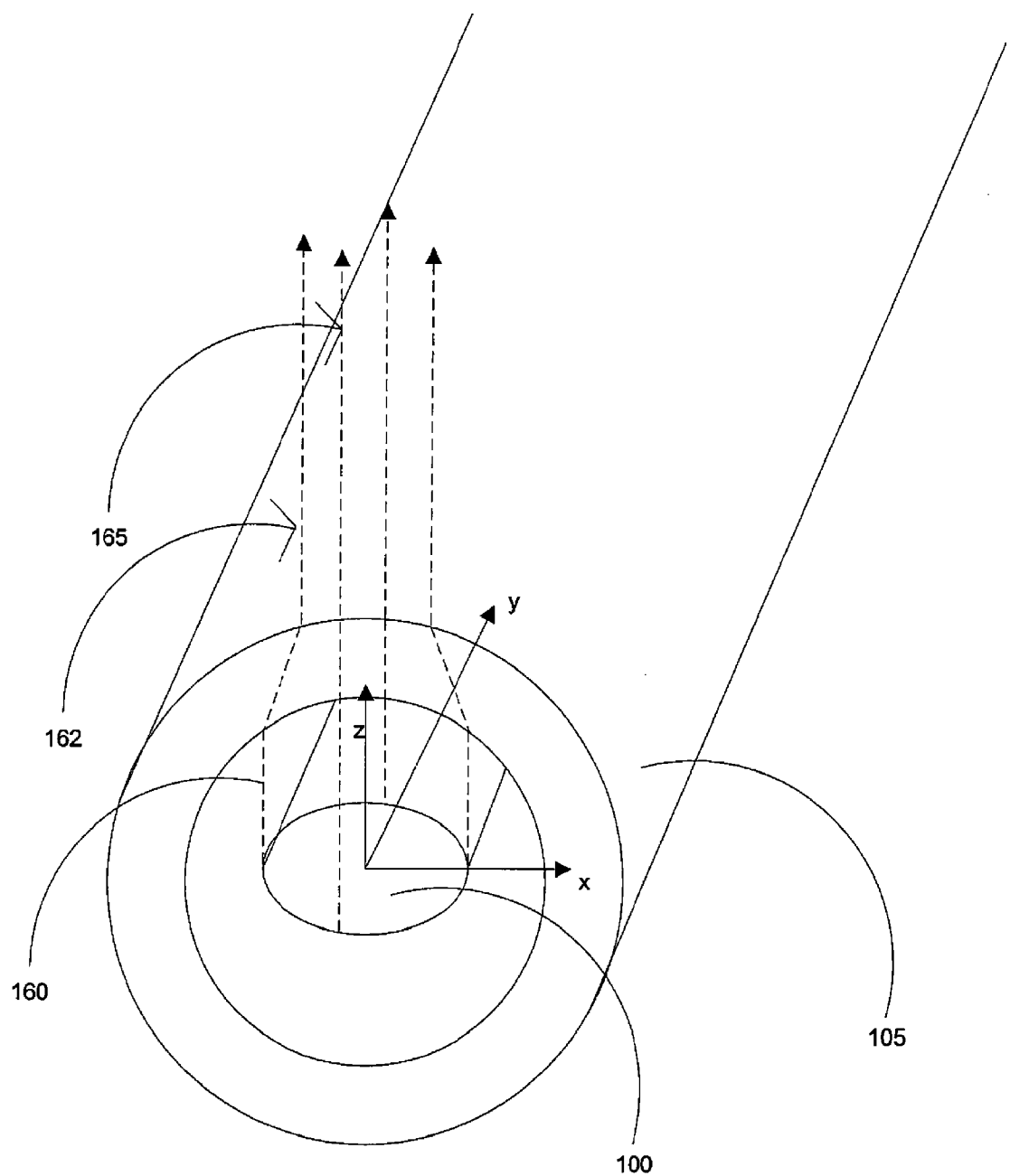
FIG. 3 is a top perspective view of an imaging transducer assembly in accordance with an example embodiment of the invention.
Figure 4A:
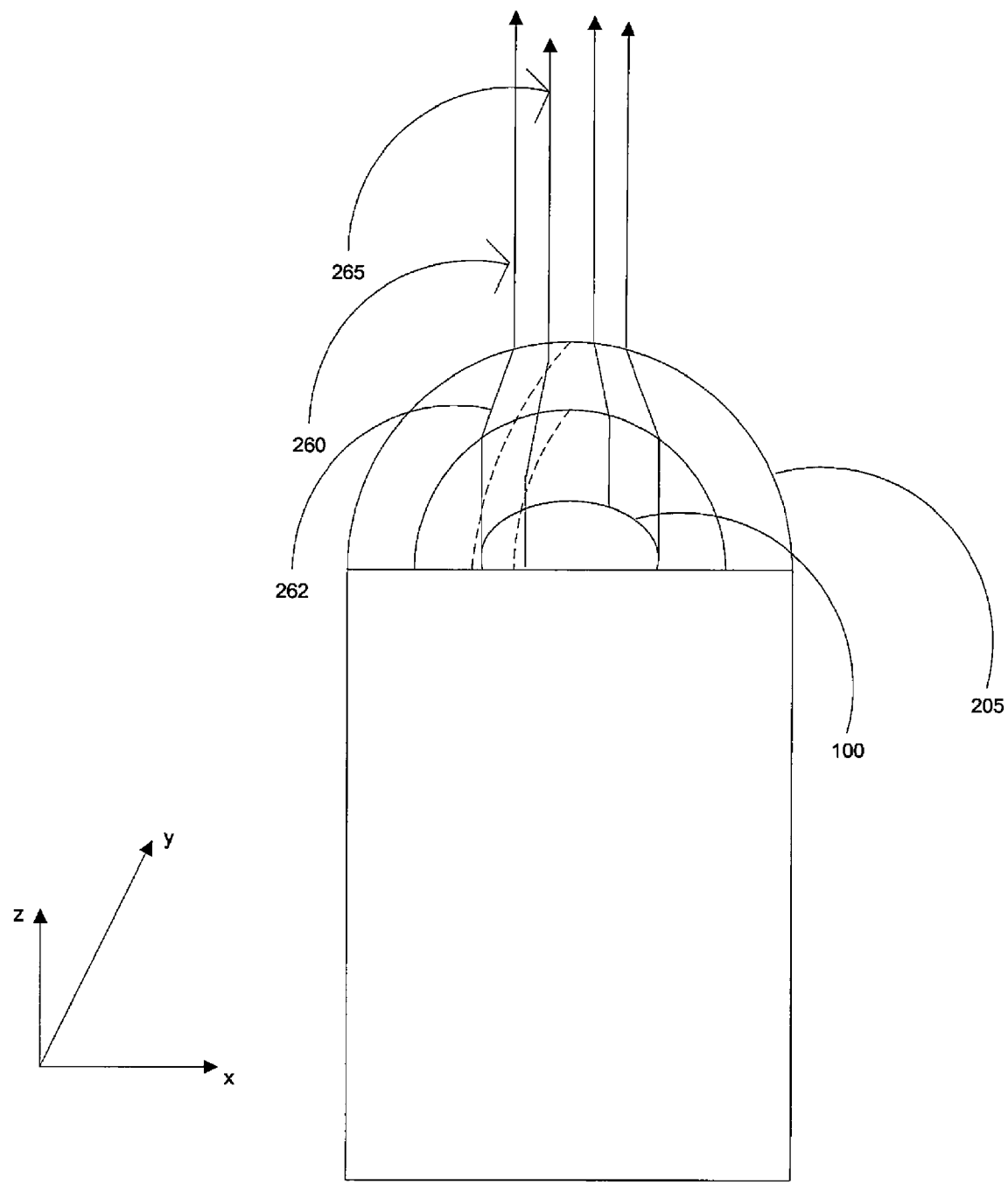
FIG. 4A is a cross-sectional side view of an imaging transducer assembly in accordance with an example embodiment of the invention.
Figure 4B:
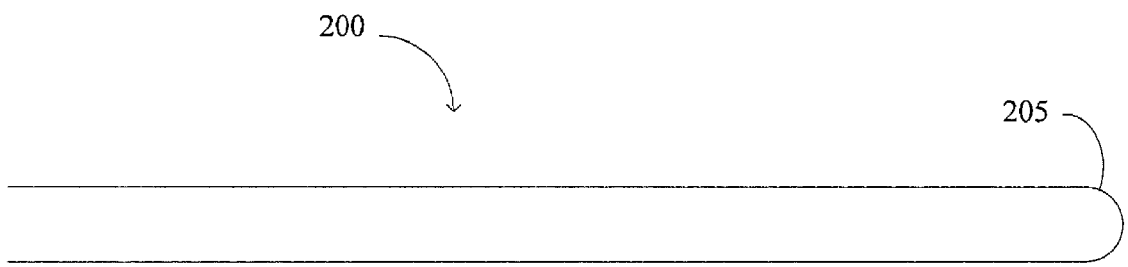
FIG. 4B is a side view of a catheter in accordance with an example embodiment of the invention.

Turning to FIG. 3, a top perspective view of the imaging transducer assembly 100 is shown. The sheath 105 has a cylindrical shape. Applying x-y-z axes, as shown, one can see that the portion 162 of the beam 160 along the x-axis is narrowed as the beam 160 exits the sheath 105. However, by virtue of the cylindrical shape, the portion 165 of the beam 160 along the y-axis may remain substantially unchanged as the beam 160 exits the sheath 105 because of the lack of curvature along the y-axis. One approach to narrowing the beam 160 along the entire perimeter of the beam 160 is shown in FIGS. 4A and 4B, which shows a cross-sectional side view of an imaging transducer assembly 100 located within the lumen of a sheath 205 having a portion of the sheath 205 that covers the assembly 100 shaped into a sphere. With the spherical shape, when the beam 260 exits the sheath 205, the surface area of the beam 260 is reduced along its entire perimeter, including the portion 262 of the beam 260 along the x-axis and the portion 265 of the beam 260 along the y-axis.

These approaches may be used individually or in any combination with other approaches mentioned above and/or with other suitable approaches to narrow the beam emitted from the assembly 100.

The above descriptions utilize a single transducer assembly 100. However, the concepts and principles described above are equally applicable to the use of multiple transducer arrays encased with acoustic beams that are steered either by mechanical rotation or electronic phasing.

Figure 5:
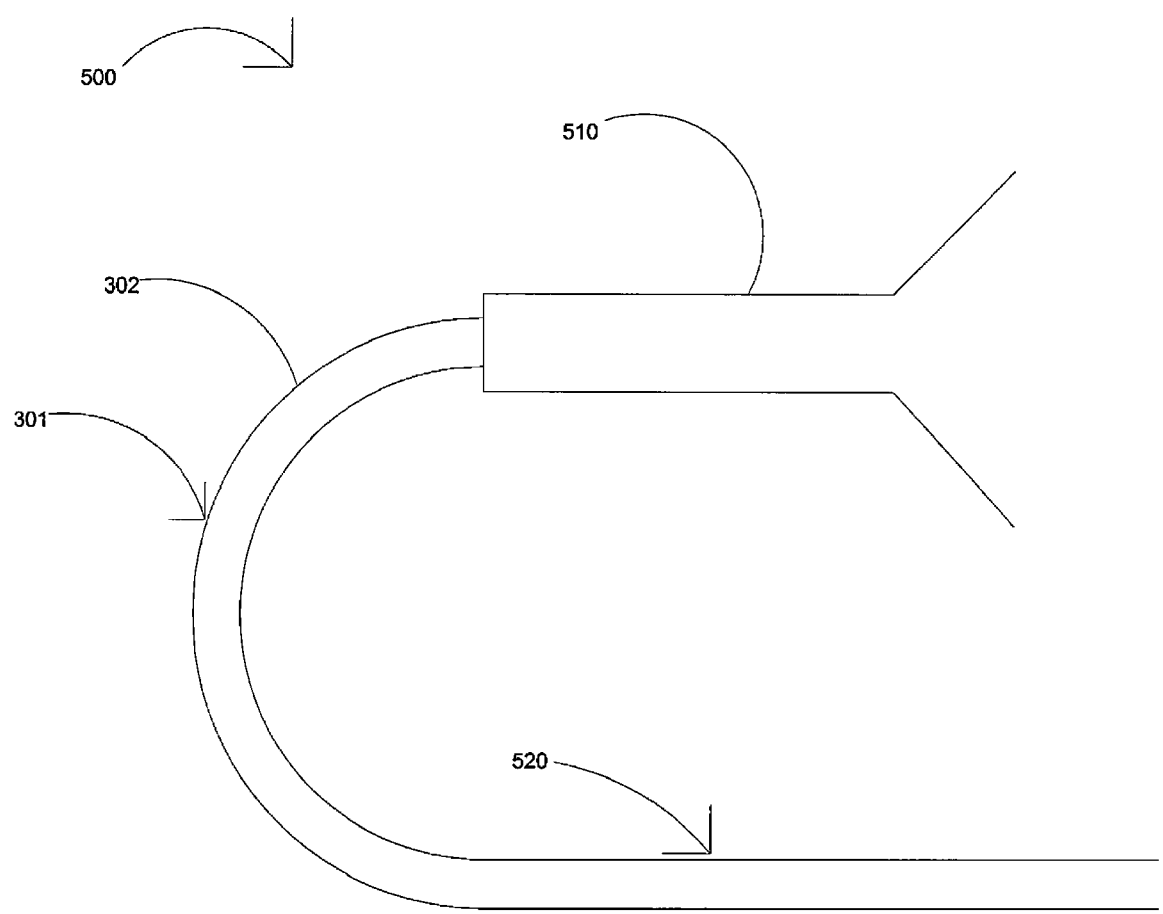
FIG. 5 is a partial cross-sectional side view of a catheter in accordance with an example embodiment of the invention.

Turning to FIG. 5, the transducer assembly 100 and one of the sheaths described above may be placed in a distal portion 520 of a guidewire 500. The guidewire 500 may comprise a guidewire body 302 in the form of a flexible, elongate tubular member, having an outer wall 301. The guidewire body 302 may be formed of any material known in the art including nitinol hypotube, metal alloys, composite materials, plastics, braided polyimide, polyethylene, peek braids, stainless steel, or other superelastic materials.

The length of the guidewire 500 may vary depending on the application. In a preferred embodiment, the length of the guidewire 500 is between 30 cm and 300 cm. A catheter (not shown) may be configured to use several different diameters of guidewires 500. For example, the guidewire 500 may have a diameter of 0.010, 0.014, 0.018, or 0.035 inches. Typically, the diameter of the guidewire 500 is uniform.

A proximal portion 510 of the guidewire 500 may be adapted to connect to circuitry (not shown) that processes imaging signals from the imaging transducer, such circuits well known in the art.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention can be performed using different or additional process actions, or a different combination or ordering of process actions. For example, this invention is particularly suited for applications involving medical imaging devices utilizing acoustic imaging devices, but can be used on any design involving imaging devices in general, such as optical or light imaging devices. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is:

1. An imaging catheter having distal and proximal ends, comprising:
    a sheath defining a lumen, the sheath being coupled to the distal end of the imaging catheter, wherein the sheath comprises a plurality of materials each having an associated phase velocity, wherein the plurality of materials are arranged into layers such that the phase velocity increases from an innermost layer to an outermost layer, wherein a medium is disposed in the lumen, the medium having a phase velocity less than the phase velocities of any of the layers of the sheath, wherein the phase velocity of the medium is less than a phase velocity of water; and
    an imaging device adapted to image a region external to the sheath by emitting a plurality of acoustic energy beams, the imaging device being located within the lumen of a distal portion of the sheath, wherein the acoustic energy beams are received, and at least partially exit the sheath to the region to be imaged.

2. The imaging catheter of claim 1, wherein the sheath is cylindrical.

3. The imaging catheter of claim 1, wherein the portion of the sheath through which the acoustic energy beams are received, and at least partially exit, is spherical.

4. The imaging catheter of claim 1, wherein the plurality of energy beams are emitted from the imaging device such that the plurality of energy beams propagate in directions that are parallel to one another until being received, and at least partially exiting the sheath to the region to be imaged.

5. The imaging catheter of claim 1, wherein the imaging device is configured and arranged to transmit the plurality of acoustic energy beams directly from the imaging device to the lumen medium, and directly from the lumen medium to the sheath.

6. The imaging catheter of claim 1, wherein the medium disposed in the lumen is a liquid.

7. The imaging catheter of claim 1, wherein the medium disposed in the lumen is an alcohol.

8. The imaging catheter of claim 1, wherein the medium disposed in the lumen is ethanol.

9. An imaging device for use within a blood vessel comprising:
    a catheter comprising a sheath defining a lumen, the lumen filled with a medium having an associated phase velocity; and
    an imaging transducer assembly configured and arranged to emit a plurality of acoustic energy beams towards a region to be imaged, at least a portion of the imaging transducer assembly located in the lumen of the sheath, the sheath comprising a plurality of materials each having an associated phase velocity, wherein the plurality of materials are arranged into layers such that the phase velocity increases from an innermost layer to an outermost layer, wherein the phase velocity of the medium disposed in the lumen is less than the phase velocities of each of the layers of the sheath, wherein the phase velocity of the medium disposed in the lumen is less than a phase velocity of water, wherein the acoustic energy beams are received, and at least partially exit the sheath to the region to be imaged, and wherein the plurality of acoustic energy beams propagate in directions that are parallel to one another substantially entirely a distance between the imaging transducer assembly and the sheath.

10. The imaging device of claim 9, wherein the sheath is cylindrical.

11. The imaging device of claim 9, wherein the portion of the sheath through which the acoustic energy beams are received, and at least partially exit, is spherical.

12. The imaging device of claim 9, wherein the imaging transducer assembly is located substantially entirely in the lumen of the sheath.

13. The imaging device of claim 9, wherein the imaging transducer is configured and arranged to transmit the plurality of acoustic energy beams directly from the imaging transducer to the lumen medium, and directly from the lumen medium to the sheath.

14. An imaging device for use in a human body, comprising:
   a catheter adapted to be inserted into the human body;
   an acoustic energy emitting means for emitting a plurality of acoustic energy beams for imaging a portion of the human body, the acoustic energy emitting means disposed in a lumen of the catheter, the lumen filled with a medium having an associated phase velocity; and
   a means for receiving the plurality of acoustic energy beams from the energy emitting means, the means for receiving the plurality of acoustic energy beams comprising a plurality of materials each having an associated phase velocity, wherein the plurality of materials are arranged into layers, wherein the phase velocity of each layer increases from an innermost layer to an outermost layer, wherein the phase velocity of the medium disposed in the lumen is less than the phase velocities of each of the layers of the means for receiving the plurality of acoustic energy beams, wherein the phase velocity of the medium disposed in the lumen is less than a phase velocity of water, wherein the acoustic energy beams are received, and at least partially exit the means for receiving the plurality of acoustic energy beams to the portion of the human body to be imaged, and wherein the plurality of acoustic energy beams propagate substantially entirely from the acoustic energy emitting means to the means for receiving the plurality of acoustic energy beams in directions that are parallel to one another.

15. The imaging device of claim 14, wherein means for receiving the plurality of acoustic energy beams is cylindrical.

16. The imaging device of claim 14, wherein the portion of means for receiving the plurality of acoustic energy beams through which the plurality of acoustic energy beams propagate is spherical.

17. The imaging device of claim 14, wherein the acoustic energy emitting means is configured and arranged to transmit the plurality of acoustic energy beams directly from the acoustic energy emitting means to the lumen medium, and directly from the lumen medium to the means for receiving the plurality of acoustic energy beams.

* * * * *